United States Patent [19]
Aguirre et al.

[11] Patent Number: 5,804,388
[45] Date of Patent: Sep. 8, 1998

[54] CHROMOSOME 9 AND PROGRESSIVE ROD-CONE DEGENERATION DISEASE GENETIC MARKERS AND ASSAYS

[75] Inventors: Gustavo Aguirre, Ithaca, N.Y.; Gregory Acland, Kennett Square, Pa.; Kunal Ray, Ithaca, N.Y.

[73] Assignee: Cornell Research Foundation, Inc., Ithaca, N.Y.

[21] Appl. No.: 891,463

[22] Filed: Jul. 10, 1997

[51] Int. Cl.[6] .............................. C12Q 1/70; C12P 19/34; C07H 21/04
[52] U.S. Cl. .............................. 435/6; 435/91.2; 435/810; 536/24.32; 536/24.33; 935/77; 935/78
[58] Field of Search .............................. 435/6, 91.2, 91.5, 435/810; 536/24.33, 24.31; 935/6, 17, 77, 78

[56] References Cited

PUBLICATIONS

Ostrander et al. Genomics 16:207–213, Apr. 1993.
Ostander et al. Mammalian Genome 6:192–195, Mar. 1995.
Petra Werner et al., "Physical and Linkage Mapping of Human Chromosome 17 Loci to Dog Chromosomes 9 and 5", 1997, Genomics, vol. 42, pp. 74–82.

*Primary Examiner*—W. Gary Jones
*Assistant Examiner*—Debra Shoemaker
*Attorney, Agent, or Firm*—Hodgson, Russ, Andrews, Woods & Goodyear

[57] ABSTRACT

Provided are nucleic acid molecules which comprise at least a portion of a polymorphic genetic marker for determining whether a canine has a mutated progressive rod-cone degeneration disease (prcd) gene locus in one or both alleles. The genetic markers are located on canine chromosome 9 in a genomic region identified as the prcd-informative region. A method for making genetic markers representing polymorphic sequences located in the prcd-informative region of canine chromosome 9 comprises isolating a polymorphic DNA sequence in the prcd-informative region, using oligonucleotides complementary with at least a portion of the sequence to amplify the sequence, and analyzing canine chromosome 9 in a prcd-informative pedigree for the ability of the polymorphic sequence to co-segregate with the prcd gene locus by a linkage test. The presence of a mutated prcd gene locus in one or both alleles of a canine in a pedigree is detected by analyzing canine chromosome 9 in the canine for the presence of at least one polymorphic genetic marker, which co-segregates with the prcd gene locus, by a linkage analysis.

39 Claims, 7 Drawing Sheets

| | P606 | | B15 | | P492 | | P432 | |
|---|---|---|---|---|---|---|---|---|
| 250 | 2 | 2 | 1 | 4 | 1 | 1 | 1 | 3 |
| 474 | 4 | 4 | 4 | 4 | 4 | 4 | 4 | 4 |
| RPD | 1 | 1 | 2 | 2 | 1 | 1 | 0 | 0 |
| 173 | 3 | 4 | 1 | 1 | 4 | 3 | 4 | 4 |
| APOH | 3 | 4 | 4 | 4 | 4 | 3 | 4 | 4 |
| MLC1 | 2 | 3 | 3 | 3 | 3 | 2 | 2 | 3 |
| 2263 | 3 | 5 | 2 | 6 | 5 | 4 | 1 | 5 |
| prcd | P | P | + | + | P | P | P | P |
| GRB2 | 0 | 0 | 0 | 0 | 0 | 0 | 0 | 0 |

| | P827 | | | | P848 | |
|---|---|---|---|---|---|---|
| 250 | 2 | 1 | | | 1 | 1 |
| 474 | 4 | 4 | | | 4 | 4 |
| RPD | 1 | 2 | | | 1 | 1 |
| 173 | 3 | 1 | | | 4 | 4 |
| APOH | 3 | 4 | | | 4 | 4 |
| MLC1 | 2 | 3 | | | 3 | 2 |
| 2263 | 3 | 2 | | | 5 | 1 |
| prcd | P | + | | | P | P |
| GRB2 | 1 | 2 | | | 1 | 1 |

| | P932 | | P936 | | P955 | | P956 | | P957 | |
|---|---|---|---|---|---|---|---|---|---|---|
| 250 | 1 | 1 | 2 | 1 | 1 | 2 | 1 | 1 | 2 | 1 |
| 474 | 4 | 4 | 4 | 4 | 4 | 4 | 4 | 4 | 4 | 4 |
| RPD | 2 | 1 | 2 | 1 | 1 | 2 | 2 | 1 | 1 | 1 |
| 173 | 1 | 4 | 1 | 4 | 4 | 1 | 1 | 4 | 3 | 4 |
| APOH | 4 | 4 | 4 | 4 | 4 | 4 | 4 | 4 | 3 | 4 |
| MLC1 | 3 | 3 | 3 | 3 | 2 | 3 | 3 | 2 | 2 | 3 |
| 2263 | 0 | 0 | 2 | 5 | 1 | 2 | 2 | 1 | 3 | 5 |
| prcd | + | P | + | P | P | + | + | P | P | P |
| GRB2 | 2 | 1 | 2 | 1 | 1 | 2 | 2 | 1 | 1 | 1 |

FIG. 5

| P780 | | H88 | |
|---|---|---|---|
| NFI | 2:2 | 3:1 | |
| 250 | =:= | 0:0 | |
| 474 | 3:- | 2:3 | |
| RARA | 1:-3 | 0:0 | |
| RPD | -:- | 1:- | |
| 173 | 2:4 | 4:2 | |
| APOH | 3:4 | 3:3 | |
| MLCI | 2:3 | 2:3 | |
| 2263 | 5:2 | 3:3 | |
| prcd | P:+ | +:+ | |
| GALK | 1:- | 2:1 | |
| GRB2 | -:2 | 0:0 | |
| TKI | 3:3 | 2:3 | |

| P703 | | P924 | | P972 | |
|---|---|---|---|---|---|
| NFI | 2:2 | 2:2 | | 2:3 | |
| 250 | 1:- | 1:- | | 0:0 | |
| 474 | 3:3 | 3:3 | | 3:2 | |
| RARA | 4:- | 1:- | | 4:2 | |
| RPD | -:- | -:- | | 0:0 | |
| 173 | 2:3 | 2:2 | | 3:2 | |
| APOH | 3:4 | 3:3 | | 4:3 | |
| MLCI | 2:3 | 2:2 | | 3:2 | |
| 2263 | 5:5 | 5:5 | | -:- | |
| prcd | P:P | P:P | | +:P | |
| GALK | -:- | -:- | | -:2 | |
| GRB2 | -:- | -:- | | -:2 | |
| TKI | -:3 | -:3 | | 3:2 | |

SEQUENCE LISTING ( 1 ) GENERAL INFORMATION:

( i i i ) NUMBER OF SEQUENCES: 31

( 2 ) INFORMATION FOR SEQ ID NO:1 :

( i ) SEQUENCE CHARACTERISTICS:
        ( A ) LENGTH: 20 nucleotides
        ( B ) TYPE: nucleic acid
        ( C ) STRANDEDNESS: single- stranded
        ( D ) TOPOLOGY: linear ( i i ) MOLECULE TYPE: DNA ( i i i ) HYPOTHETICAL: No ( i v ) SEQUENCE DESCRIPTION: SEQ ID NO:1 :

ATCCAGGTCT GGAATACCCC 20

( 2 ) INFORMATION FOR SEQ ID NO:2 :

( i ) SEQUENCE CHARACTERISTICS:
        ( A ) LENGTH: 21 nucleotides
        ( B ) TYPE: nucleic acid
        ( C ) STRANDEDNESS: single- stranded
        ( D ) TOPOLOGY: linear ( i i ) MOLECULE TYPE: DNA ( i i i ) HYPOTHETICAL: No ( i v ) SEQUENCE DESCRIPTION: SEQ ID NO:2 :

TCCTTTGAAT TAGCACTTGG C 21

( 2 ) INFORMATION FOR SEQ ID NO:3 :

( i ) SEQUENCE CHARACTERISTICS:
        ( A ) LENGTH: 22 nucleotides
        ( B ) TYPE: nucleic acid
        ( C ) STRANDEDNESS: single- stranded
        ( D ) TOPOLOGY: linear ( i i ) MOLECULE TYPE: DNA ( i i i ) HYPOTHETICAL: No ( i v ) SEQUENCE DESCRIPTION: SEQ ID NO:3 :

TTAAGCCTTA TTTTGTGTTG GG 22

( 2 ) INFORMATION FOR SEQ ID NO:4 :

( i ) SEQUENCE CHARACTERISTICS:
        ( A ) LENGTH: 19 nucleotides
        ( B ) TYPE: nucleic acid
        ( C ) STRANDEDNESS: single- stranded
        ( D ) TOPOLOGY: linear ( i i ) MOLECULE TYPE: DNA ( i i i ) HYPOTHETICAL: No ( i v ) SEQUENCE DESCRIPTION: SEQ ID NO:4 :

TCCAGGAAGT GTCTGCAGG 19

( 2 ) INFORMATION FOR SEQ ID NO:5 :

( i ) SEQUENCE CHARACTERISTICS:
        ( A ) LENGTH: 20 nucleotides (B) TYPE: nucleic acid
              (C) STRANDEDNESS: single-stranded
              (D) TOPOLOGY: linear (ii) MOLECULE TYPE: DNA (iii) HYPOTHETICAL: No (iv) SEQUENCE DESCRIPTION: SEQ ID NO:5:

TTAGTTAACC CAGCTCCCCA                                           20

(2) INFORMATION FOR SEQ ID NO:6:

(i) SEQUENCE CHARACTERISTICS:
              (A) LENGTH: 20 nucleotides
              (B) TYPE: nucleic acid
              (C) STRANDEDNESS: single-stranded
              (D) TOPOLOGY: linear (ii) MOLECULE TYPE: DNA (iii) HYPOTHETICAL: No (iv) SEQUENCE DESCRIPTION: SEQ ID NO:6:

TCACCCTGTT AGCTGCTCAA                                           20

(2) INFORMATION FOR SEQ ID NO:7:

(i) SEQUENCE CHARACTERISTICS:
              (A) LENGTH: 25 nucleotides
              (B) TYPE: nucleic acid
              (C) STRANDEDNESS: single-stranded
              (D) TOPOLOGY: linear (ii) MOLECULE TYPE: DNA (iii) HYPOTHETICAL: No (iv) SEQUENCE DESCRIPTION: SEQ ID NO:7:

CATGTAGAGT GATTAGTTGG TCTTT                                     25

(2) INFORMATION FOR SEQ ID NO:8:

(i) SEQUENCE CHARACTERISTICS:
              (A) LENGTH: 20 nucleotides
              (B) TYPE: nucleic acid
              (C) STRANDEDNESS: single-stranded
              (D) TOPOLOGY: linear (ii) MOLECULE TYPE: DNA (iii) HYPOTHETICAL: No (iv) SEQUENCE DESCRIPTION: SEQ ID NO:8:

CTGAATATCC TCTGCCCTTC                                           20

(2) INFORMATION FOR SEQ ID NO:9:

(i) SEQUENCE CHARACTERISTICS:
              (A) LENGTH: 21 nucleotides
              (B) TYPE: nucleic acid
              (C) STRANDEDNESS: single-stranded
              (D) TOPOLOGY: linear (ii) MOLECULE TYPE: DNA (iii) HYPOTHETICAL: No (iv) SEQUENCE DESCRIPTION: SEQ ID NO:9:

TCTGGGACAA AGCTTGGCAT G                                         21

( 2 ) INFORMATION FOR SEQ ID NO:10 :

( i ) SEQUENCE CHARACTERISTICS:
        ( A ) LENGTH: 25 nucleotides
        ( B ) TYPE: nucleic acid
        ( C ) STRANDEDNESS: single- stranded
        ( D ) TOPOLOGY: linear ( i i ) MOLECULE TYPE: DNA ( i i i ) HYPOTHETICAL: No ( i v ) SEQUENCE DESCRIPTION: SEQ ID NO:10 :

GCCTTTGCTC ATAAGGCACA TAAGC     25

( 2 ) INFORMATION FOR SEQ ID NO:11 :

( i ) SEQUENCE CHARACTERISTICS:
        ( A ) LENGTH: 23 nucleotides
        ( B ) TYPE: nucleic acid
        ( C ) STRANDEDNESS: single- stranded
        ( D ) TOPOLOGY: linear ( i i ) MOLECULE TYPE: DNA ( i i i ) HYPOTHETICAL: No ( i v ) SEQUENCE DESCRIPTION: SEQ ID NO:11 :

CTTTGCTCCA CATAAGAAGC TGT     23

( 2 ) INFORMATION FOR SEQ ID NO:12 :

( i ) SEQUENCE CHARACTERISTICS:
        ( A ) LENGTH: 21 nucleotides
        ( B ) TYPE: nucleic acid
        ( C ) STRANDEDNESS: single- stranded
        ( D ) TOPOLOGY: linear ( i i ) MOLECULE TYPE: DNA ( i i i ) HYPOTHETICAL: No ( i v ) SEQUENCE DESCRIPTION: SEQ ID NO:12 :

CATTTTCCTT CCTCGGTGCA T     21

( 2 ) INFORMATION FOR SEQ ID NO:13 :

( i ) SEQUENCE CHARACTERISTICS:
        ( A ) LENGTH: 24 nucleotides
        ( B ) TYPE: nucleic acid
        ( C ) STRANDEDNESS: single- stranded
        ( D ) TOPOLOGY: linear ( i i ) MOLECULE TYPE: DNA ( i i i ) HYPOTHETICAL: No ( i v ) SEQUENCE DESCRIPTION: SEQ ID NO:13 :

GCATTACAAA ATAGGGGGAA AGGC     24

( 2 ) INFORMATION FOR SEQ ID NO:14 :

( i ) SEQUENCE CHARACTERISTICS:
        ( A ) LENGTH: 25 nucleotides
        ( B ) TYPE: nucleic acid
        ( C ) STRANDEDNESS: single- stranded
        ( D ) TOPOLOGY: linear ( i i ) MOLECULE TYPE: DNA ( i i i ) HYPOTHETICAL: No ( i v ) SEQUENCE DESCRIPTION: SEQ ID NO:14 :

CATTGTTTGA CCGGACCCCG ACTGG                                                                         25

( 2 ) INFORMATION FOR SEQ ID NO:15 :

( i ) SEQUENCE CHARACTERISTICS:
        ( A ) LENGTH: 23 nucleotides
        ( B ) TYPE: nucleic acid
        ( C ) STRANDEDNESS: single- stranded
        ( D ) TOPOLOGY: linear ( i i ) MOLECULE TYPE: DNA ( i i i ) HYPOTHETICAL: No ( i v ) SEQUENCE DESCRIPTION: SEQ ID NO:15 :

CCTTGTTGCG GGAAATGTGC TGC                                                                           23

( 2 ) INFORMATION FOR SEQ ID NO:16 :

( i ) SEQUENCE CHARACTERISTICS:
        ( A ) LENGTH: 23 nucleotides
        ( B ) TYPE: nucleic acid
        ( C ) STRANDEDNESS: single- stranded
        ( D ) TOPOLOGY: linear ( i i ) MOLECULE TYPE: DNA ( i i i ) HYPOTHETICAL: No ( i v ) SEQUENCE DESCRIPTION: SEQ ID NO:16 :

GTGCAGCACT TCAAGGTGCT CCG                                                                           23

( 2 ) INFORMATION FOR SEQ ID NO:17 :

( i ) SEQUENCE CHARACTERISTICS:
        ( A ) LENGTH: 23 nucleotides
        ( B ) TYPE: nucleic acid
        ( C ) STRANDEDNESS: single- stranded
        ( D ) TOPOLOGY: linear ( i i ) MOLECULE TYPE: DNA ( i i i ) HYPOTHETICAL: No ( i v ) SEQUENCE DESCRIPTION: SEQ ID NO:17 :

GTGGCCTTAA ACGTCATGCA CTG                                                                           23

( 2 ) INFORMATION FOR SEQ ID NO:18 :

( i ) SEQUENCE CHARACTERISTICS:
        ( A ) LENGTH: 22 nucleotides
        ( B ) TYPE: nucleic acid
        ( C ) STRANDEDNESS: single- stranded
        ( D ) TOPOLOGY: linear ( i i ) MOLECULE TYPE: DNA ( i i i ) HYPOTHETICAL: No ( i v ) SEQUENCE DESCRIPTION: SEQ ID NO:18 :

AGAATAGGGC AGATCAGTAC TT                                                                            22

( 2 ) INFORMATION FOR SEQ ID NO:19 :

( i ) SEQUENCE CHARACTERISTICS:
        ( A ) LENGTH: 19 nucleotides
        ( B ) TYPE: nucleic acid
        ( C ) STRANDEDNESS: single- stranded ( D ) TOPOLOGY: linear ( i i ) MOLECULE TYPE: DNA ( i i i ) HYPOTHETICAL: No ( i v ) SEQUENCE DESCRIPTION: SEQ ID NO:19 :

AGAATAGGGC CACAGAACT                                                                                                19

( 2 ) INFORMATION FOR SEQ ID NO:20 :

( i ) SEQUENCE CHARACTERISTICS:
                    ( A ) LENGTH: 20 nucleotides
                    ( B ) TYPE: nucleic acid
                    ( C ) STRANDEDNESS: single- stranded
                    ( D ) TOPOLOGY: linear ( i i ) MOLECULE TYPE: DNA ( i i i ) HYPOTHETICAL: No ( i v ) SEQUENCE DESCRIPTION: SEQ ID NO:20 :

TCCCAGCTCA GAGTCTGTTC                                                                                               20

( 2 ) INFORMATION FOR SEQ ID NO:21 :

( i ) SEQUENCE CHARACTERISTICS:
                    ( A ) LENGTH: 24 nucleotides
                    ( B ) TYPE: nucleic acid
                    ( C ) STRANDEDNESS: single- stranded
                    ( D ) TOPOLOGY: linear ( i i ) MOLECULE TYPE: DNA ( i i i ) HYPOTHETICAL: No ( i v ) SEQUENCE DESCRIPTION: SEQ ID NO:21 :

GGTGCATTTA GCAGAGCTAC TTCC                                                                                          24

( 2 ) INFORMATION FOR SEQ ID NO:22 :

( i ) SEQUENCE CHARACTERISTICS:
                    ( A ) LENGTH: 23 nucleotides
                    ( B ) TYPE: nucleic acid
                    ( C ) STRANDEDNESS: single- stranded
                    ( D ) TOPOLOGY: linear ( i i ) MOLECULE TYPE: DNA ( i i i ) HYPOTHETICAL: No ( i v ) SEQUENCE DESCRIPTION: SEQ ID NO:22 :

CTTCCCCCTC TGCCTGTGTC TCT                                                                                           23

( 2 ) INFORMATION FOR SEQ ID NO:23 :

( i ) SEQUENCE CHARACTERISTICS:
                    ( A ) LENGTH: 24 nucleotides
                    ( B ) TYPE: nucleic acid
                    ( C ) STRANDEDNESS: single- stranded
                    ( D ) TOPOLOGY: linear ( i i ) MOLECULE TYPE: DNA ( i i i ) HYPOTHETICAL: No ( i v ) SEQUENCE DESCRIPTION: SEQ ID NO:23 :

ATCGCTAATT CATGCCCTTG TGGT                                                                                          24

( 2 ) INFORMATION FOR SEQ ID NO:24 :

( i ) SEQUENCE CHARACTERISTICS:
   ( A ) LENGTH: 24 nucleotides
   ( B ) TYPE: nucleic acid
   ( C ) STRANDEDNESS: single-stranded
   ( D ) TOPOLOGY: linear ( i i ) MOLECULE TYPE: DNA ( i i i ) HYPOTHETICAL: No ( i v ) SEQUENCE DESCRIPTION: SEQ ID NO:24 :

AATTGAGTTT TTGGGGTGCC TGAG    24

( 2 ) INFORMATION FOR SEQ ID NO:25 :

( i ) SEQUENCE CHARACTERISTICS:
      ( A ) LENGTH: 24 nucleotides
      ( B ) TYPE: nucleic acid
      ( C ) STRANDEDNESS: single-stranded
      ( D ) TOPOLOGY: linear ( i i ) MOLECULE TYPE: DNA ( i i i ) HYPOTHETICAL: No ( i v ) SEQUENCE DESCRIPTION: SEQ ID NO:25 :

CAATGAGCTG AGATGGTGTA GTAG    24

( 2 ) INFORMATION FOR SEQ ID NO:26 :

( i ) SEQUENCE CHARACTERISTICS:
      ( A ) LENGTH: 18 nucleotides
      ( B ) TYPE: nucleic acid
      ( C ) STRANDEDNESS: single-stranded
      ( D ) TOPOLOGY: linear ( i i ) MOLECULE TYPE: DNA ( i i i ) HYPOTHETICAL: No ( i v ) SEQUENCE DESCRIPTION: SEQ ID NO:26 :

CAGGGCAGGG CGGGTCAT    18

( 2 ) INFORMATION FOR SEQ ID NO:27 :

( i ) SEQUENCE CHARACTERISTICS:
      ( A ) LENGTH: 24 nucleotides
      ( B ) TYPE: nucleic acid
      ( C ) STRANDEDNESS: single-stranded
      ( D ) TOPOLOGY: linear ( i i ) MOLECULE TYPE: DNA ( i i i ) HYPOTHETICAL: No ( i v ) SEQUENCE DESCRIPTION: SEQ ID NO:27 :

GAAGATCTGA AGAACTTAGA GGAG    24

( 2 ) INFORMATION FOR SEQ ID NO:28 :

( i ) SEQUENCE CHARACTERISTICS:
      ( A ) LENGTH: 20 nucleotides
      ( B ) TYPE: nucleic acid
      ( C ) STRANDEDNESS: single-stranded
      ( D ) TOPOLOGY: linear ( i i ) MOLECULE TYPE: DNA ( i i i ) HYPOTHETICAL: No ( i v ) SEQUENCE DESCRIPTION: SEQ ID NO:28 :

```
TCCCAAGTGA CCGTTAGAGC                                                                           20
```

( 2 ) INFORMATION FOR SEQ ID NO:29 :

( i ) SEQUENCE CHARACTERISTICS:
        ( A ) LENGTH: 19 nucleotides
        ( B ) TYPE: nucleic acid
        ( C ) STRANDEDNESS: single- stranded
        ( D ) TOPOLOGY: linear ( i i ) MOLECULE TYPE: DNA ( i i i ) HYPOTHETICAL: No ( i v ) SEQUENCE DESCRIPTION: SEQ ID NO:29 :

```
CCAGTGCCAG GGAGAGTTT                                                                            19
```

( 2 ) INFORMATION FOR SEQ ID NO:30 :

( i ) SEQUENCE CHARACTERISTICS:
        ( A ) LENGTH: 22 nucleotides
        ( B ) TYPE: nucleic acid
        ( C ) STRANDEDNESS: single- stranded
        ( D ) TOPOLOGY: linear ( i i ) MOLECULE TYPE: DNA ( i i i ) HYPOTHETICAL: No ( i v ) SEQUENCE DESCRIPTION: SEQ ID NO:30 :

```
GAATGAGTCA TATGGTGAGC CA                                                                        22
```

( 2 ) INFORMATION FOR SEQ ID NO:31 :

( i ) SEQUENCE CHARACTERISTICS:
        ( A ) LENGTH: 21 nucleotides
        ( B ) TYPE: nucleic acid
        ( C ) STRANDEDNESS: single- stranded
        ( D ) TOPOLOGY: linear ( i i ) MOLECULE TYPE: DNA ( i i i ) HYPOTHETICAL: No ( i v ) SEQUENCE DESCRIPTION: SEQ ID NO:31 :

```
ACAATGGAGT GGCAACTGTG A                                                                         21
```

CHROMOSOME 9 AND PROGRESSIVE ROD-CONE DEGENERATION DISEASE GENETIC MARKERS AND ASSAYS

FIELD OF THE INVENTION

The present invention relates generally to a class of genetic diseases, observed in canines, termed progressive rod-cone degeneration ("prcd"). More particularly, the invention relates to molecular markers, and a method of using the molecular markers, for identifying the prcd gene locus and mutations thereof responsible for progressive rod-cone degeneration in canines.

BACKGROUND OF THE INVENTION

1. The Disease

Progressive retinal atrophy in canines is a group of diseases which are typically inherited by means of an autosomal recessive gene defect. This group of diseases have similar clinical features that include: initial night blindness followed by reduction in photopic vision leading to complete blindness; reduction in retinal vessels, and retinal thinning; abnormalities in an electroretinogram ("ERG"); and the development of cataracts. A specific class of progressive retinal atrophy in canines is the recessively inherited, late-onset retinal degenerations, including diseases involving photoreceptor cell degeneration.

Mutations at the prcd gene locus account for all of the autosomal recessive late-onset hereditary retinal degenerations recognized to date in dogs. By cross-breeding experiments, it has been determined that the prcd gene locus is responsible for progressive retinal atrophy in poodles (toy, miniature, and standard), cocker spaniels (American, and English), Labrador retrievers, and Portuguese water dogs (see, e.g., Aguirre and Acland, 1988, *Exp. Eye Res.* 46:663–687; 1991, *Invest. Ophthalmol. Vis. Sci.* (Supp). 32). However, based on clinical and genetic parameters consistent with disease caused by mutations at the prcd gene locus, other breeds of dogs suspected of having prcd as the form of observed progressive retinal atrophy include akita, Australian cattle dog, basenji, border collie, Chesapeake bay retriever, English mastiff, English springer spaniel, havanese, lowchen, Nova scotia duck tolling retriever, papillon, samoyed, standard wirehaired dachshund, and Tibetan terriers. Depending on the breed of the dog, different mutations responsible for allelic variants of the prcd gene locus can regulate the rate of progression, but not the phenotype, of photoreceptor degeneration (unpublished observations of the present inventors).

2. Detection of Carriers—A Problem in Breeding

Diagnosis of breeds affected with the prcd group of diseases is complicated by the need for sophisticated testing methods such as ERG, and by the late onset of the disease. Regarding the latter, the age by which the disease can be diagnosed by current methods may be an age which is later than the dog's reproductive life. For example, in English cocker spaniels, progressive retinal atrophy may be diagnosed by ERG at three years of age, and by ophthalmoscopy at 5–8 years of age. This late age of diagnosis results in the dissemination of the undesirable trait within the population, and an increase in the disease frequency.

Estimates of the frequency of progressive rod-cone degeneration may vary depending upon the breed affected. It is believed that approximately 2% of Labrador retrievers older than 2 to 3 years of age are affected with progressive rod-cone degeneration. In the population of Labrador retrievers, an estimated carrier frequency of mutations at the prcd gene locus could be as high as 24%. In poodles and cocker spaniels, the disease rate is higher than that observed in Labrador retrievers, and hence, the carrier rate would be expected to be higher. From the results of a survey of Portuguese water dogs, the calculated carrier frequency is approximately 40%.

The only effective control measure now available to dog breeders is to perform "test" matings to identify carrier dogs, and to eliminate the identified carriers from breeding programs, thereby reducing the frequency of genetic disease in a breed. In a test mating, the dog being evaluated as a potential carrier of the genetic disease is mated with a dog known to be affected with the disease. Progeny are then observed for absence or presence of the disease, and a litter of unaffected offspring typically "clears" the dog from being a carrier. While test matings have been effectively used for breeds having large litter sizes, and for diseases which are early onset, such a procedure is not practical for reducing the frequency of prcd. In addition to the disadvantages of test matings such as great expenses in time and effort incurred to clear a dog and that affected dogs can be born if the dog to be evaluated is a carrier, test matings are not particularly suited for detection of carriers of prcd because of the late onset of clinical symptoms associated with the disease, and because some of the breeds affected have small litters (too small for establishing statistical probability).

Thus, there is a long felt need in the canine breeding industry for a genetic test that permits the identification of and in various breeds of dogs that have the prcd form of progressive retinal atrophy (e.g., before detectable onset of clinical symptoms), as well as permitting the genotyping of dogs at risk for prcd.

3. Linkage tests

For any single gene disorder such as prcd, identification of the defective gene can allow for screening of the at-risk population to identify carriers in an effort to reduce the frequency of the single gene disorder in that population. Until the identification of the specific gene mutations responsible for the disease, a useful diagnostic alternative is a test based on linkage analysis. Linkage analysis is based on first finding the general chromosomal region in which the mutated gene is located, followed by identification of genetic markers to characterize a much smaller region of the chromosome containing the disease locus (the location of the mutated gene). The closer together the marker and the mutated gene are on the chromosome, the less likely a recombination event will occur between them during meioses; i.e., there is linkage between the marker and the prcd gene. The more closely linked the marker and mutated gene are, the more predictive and useful is the test for identifying carriers. Additionally, by using two or more marker loci, substantial additional information can be ascertained in a linkage analysis that can markedly increase the accuracy of the linkage test. Further, using multiple marker loci in a linkage analysis allows for the ability to screen various affected breeds of dogs to identify breed-specific haplotypes that characterize the prcd allele in the specific breed of dog. Currently, the only linkage test available for dogs is a single microsatellite marker test for copper toxicosis (Yuzbasiyan-Gurkan et al., 1997, *Am. J. Vet. Res.* 1997 58:23–27).

SUMMARY OF THE INVENTION

In the development of the present invention, the prcd gene locus was mapped to regions within canine chromosome 9 including genes analogous to human genes mapping to human chromosome 17 within, approximate, or distal to band q21-25; and to the centromeric end of chromosome 9. Thus, localization of the prcd gene locus to canine genes mapping to chromosome 9, and the identification and development of multiple primers/markers linked to these genomic regions, provides methods and compositions for identifying sequence variations in these genomic regions that can be used to identify between dogs affected with prcd and those dogs that are not affected. The markers and assays of the present invention allow for the identification of prcd gene locus mutant alleles that occur in several breeds of dogs, thus detecting pedigree specific prcd-linked polymorphisms. Further, because of the close proximity of at least one of the markers to the prcd gene locus (0.0 recombination), a disease specific haplotype may be identified for each prcd-affected breed.

BRIEF DESCRIPTION OF THE FIGURES

FIG. 2 shows the results of a cross between a prcd-affected parent dog with a prcd-carrier parent dog, including the status of the progeny.

FIG. 3 shows the results of a cross between a prcd-affected parent dog with a prcd-carrier parent dog, including the status of the progeny.

FIG. 4 shows the results of a cross between a prcd-affected parent dog with a prcd-carrier parent dog, including the status of the progeny.

FIG. 5 shows the results of a cross between a prcd-affected parent dog with a prcd-carrier parent dog, including the status of the progeny.

FIG. 6 shows the results of a cross between a prcd-affected parent dog with a prcd-carrier parent dog, including the status of the progeny.

DETAILED DESCRIPTION OF THE INVENTION

Definitions

Figure 1:
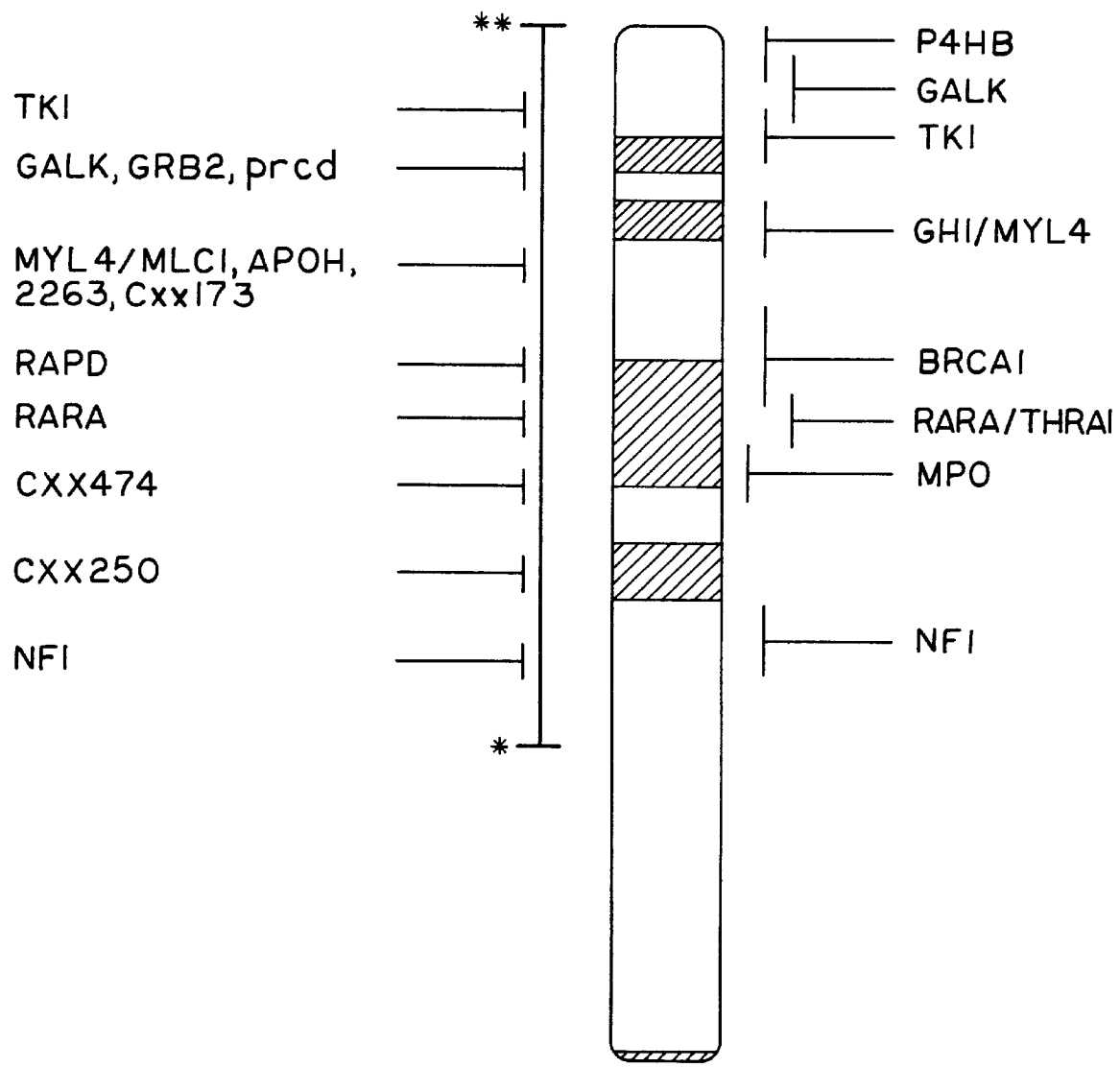
FIG. 1 is a genetic map of canine chromosome 9 with the prcd-informative region of the chromosome, and genetic markers therein useful in identification of prcd gene locus, shown along the left.

"prcd" is a term used hereinafter for the purposes of the specification and claims to refer to progressive rod-cone degenerations, a group of autosomal recessive late-onset hereditary retinal degenerations in canines caused by mutations at the prcd gene locus (Aguirre and Acland, 1988, *Exp. Eye Res.* 46:663–687). Clinical features of prcd include initial night blindness followed by reduction in photopic vision leading to complete blindness; reduction in retinal vessels, and retinal thinning; abnormalities in an electroretinogram ("ERG"); and the development of cataracts. On canine chromosome 9, the prcd gene locus comprises genomic regions within canine genes (see FIG. 1) which are analogous to genes mapping to human chromosome 17 within, approximate, or distal to band q21–25, and to the centromeric end of canine chromosome 9. However, note that those analogous regions on canine chromosome 9 are inverted entirely in respect to human chromosome 17.

"LOD score" (also referred to as "Zmax") is a term used hereinafter for the purposes of the specification and claims to refer to an indicated probability (the logarithm of the ratio of the likelihood) that a genetic marker locus and the prcd gene locus are linked at a particular distance. For example, a total LOD score of greater than 3.0 is considered to be significant evidence for linkage between the two loci at that particular recombination fraction. A LOD score of 3.0 corresponds statistically to a less than 5% error rate (e.g., less than a 5% probability of having achieved the observed recombination fraction by chance).

"Recombination fraction" or "RF" is a term used hereinafter for the purposes of the specification and claims to refer to an estimate of the linkage distance between two genetic loci, which statistically, is the maximal likelihood estimate of the true recombination distance, theta ($\theta$). For example, with perfect segregation of chromosomes, an RF=0.0 would indicate that the genetic marker locus and the prcd gene locus has segregated together because they are closely linked; i.e., no recombination has occurred between the genetic marker locus and the prcd gene locus.

"Genetic marker" or "marker" is a term used hereinafter for the purposes of the specification and claims to refer to a variable nucleotide sequence (polymorphic) that is present in canine genomic DNA on chromosome 9, and which is identifiable with specific oligonucleotides (e.g., distinguishable by nucleic acid amplification and observance of a difference in size or sequence of nucleotides due to the polymorphism). The "locus" of a genetic marker or marker refers to its situs on the chromosome in relation to another locus as, for example, represented by LOD score and recombination fraction. Markers, as illustrated herein, can be identified by any one of several techniques know to those skilled in the art, including microsatellite or short tandem repeat (STR) amplification, analyses of restriction fragment length polymorphisms (RFLP), single nucleotide polymorphism (SNP), detection of deletion or insertion sites, and random amplified polymorphic DNA (RAPD) analysis (Cushwa and Medrano, 1996, *Animal Biotech.* 7:11–31). "Genetic marker indicative of a mutation in the prcd gene locus" refers to a marker that: (a) is genetically linked and co-segregates with the prcd gene locus such that the linkage observed has a LOD score of at least 3.0; (b) comprises a region of canine chromosome 9 which is analogous to a gene or noncoding region mapping to human chromosome 17 within or approximate to band q21 to band q25, or distal to band q25, and extending to the centromeric end of chromosome 9 (the prcd-informative region; see FIG. 1); (c) contains a polymorphism informative for the prcd genotype; and (d) can be used in a linkage assay or other molecular diagnostic assays (DNA test) to identify normal alleles (wild type; (+)), and mutant (prcd) alleles (by the presence of the polymorphism), and hence can distinguish prcd affected dogs (prcd/prcd), carriers of prcd (prcd/+), and normal dogs (+/+). In that regard, markers additional to those illustrative examples disclosed herein, that map either by linkage or by physical methods so close to the prcd gene locus that any polymorphism in or with such derivative chromosomal regions, may be used in a molecular diagnostic assay for detection of prcd or the carrier status.

"Co-segregate" is a term used hereinafter for the purposes of the specification and claims to refer to inheritance together of two specific loci; e.g., the loci are located so physically close on the same chromosome that the rate of genetic recombination between the loci is as low as 0%, as observed by statistical analysis of inheritance patterns of alleles in a mating.

"Linkage" is a term used hereinafter for the purposes of the specification and claims to refer to co-segregation of two loci in the canine breed analyzed. Statistically significant linkage between two loci is expressed by a LOD score of 3 or greater.

"Linkage test" and "molecular diagnostic assay" are terms used hereinafter for the purposes of the specification and claims to refer to a method for determining the presence or absence of one or more allelic variants linked with the prcd gene locus, such that the method may be used for the detection of prcd or carrier status, whether through statistical probability or by actual detection of a mutated prcd gene.

"Pedigree" is a term used hereinafter for the purposes of the specification and claims to refer to a family tree.

"Polymorphism" is a term used hereinafter for the purposes of the specification and claims to refer to a marker that is distinguishably different (e.g., in size, electrophoretic migration, nucleotide sequence, ability to specifically hybridize to an oligonucleotide under standard conditions) as compared to an analogous region from a dog of the same breed or pedigree.

"Nucleic acid amplification" or "amplify" is meant, for the purposes of the specification or claims, to refer to a process by which nucleic acid sequences are amplified in number. There are several means known to those skilled in the art for enzymatically amplifying nucleic acid sequences including polymerase chain reaction ("PCR"), ligase chain reaction (LCR), and nucleic acid sequence-based amplification (NASBA).

"Hybridization" is meant, for the purposes of the specification or claims, a sufficient number of complementary base pairs in its sequence to interact specifically (hybridize) with the target nucleic acid sequence to be amplified or detected. As known to those skilled in the art, a very high degree of complementarily is needed for specificity and sensitivity involving hybridization, although it need not be 100%. Thus, for example, an oligonucleotide which is identical in nucleotide sequence to an oligonucleotide disclosed herein, except for one or two base changes or substitution, may function equivalently to the disclosed oligonucleotides.

"Consisting essentially of a nucleotide sequence" is meant, for the purposes of the specification or claims to refer to the nucleotide sequence disclosed, and also encompasses nucleotide sequences which are identical in sequence except for a one base change or substitution therein while retaining the same ability to function to detect prcd or a carrier status of a mutated prcd.

The present invention provides isolated nucleic acid molecules which comprise at least a portion of a genetic marker, and methods of using genetic markers, for determining whether a canine has a mutated prcd gene locus in one or both alleles. The genetic markers are located on canine chromosome 9, in genomic regions that are analogous to genes or noncoding regions mapping to human chromosome 17 in the general area of band q21 to band q25, and distal to band q25 to the centromeric end. The region of canine chromosome 9 containing genetic markers that are useful in the method of the present invention ("prcd-informative region") is indicated in FIG. 1. Information about exemplary nucleic acid molecules that can be used as genetic markers in the method of the present invention is provided below in Table 1. It will be appreciated and understood by those skilled in the art that with the identification of this region of canine chromosome 9 containing markers useful in the method of the present invention, and with the disclosure of exemplary genetic markers and the mapping of such markers to the prcd-informative region, additional markers useful with the method of the present invention can be identified by routine linkage mapping as described in more detail below. In that regard, also provided herein is a method for making genetic markers representing sequences located in the prcd-informative region of canine chromosome 9 which can be used for determining whether a canine has a mutated prcd gene locus in one or both alleles.

It is also important to note that using the compositions and the diagnostic method of the present invention, hereditary retinal disorders other than prcd, are not allelic with prcd. These other diseases include rod dysplasia (e.g., in the Norwegian Elkhound), rod cone dysplasia type 1 (e.g., in Irish setters); cone degeneration (e.g., in the Alaskan Malamute), and early retinal degeneration (e.g., in the Norwegian Elkhound). Consistently in all these breeds, although the disease inheritance is autosomal recessive, the onset of disease is classified as early, and the genetic locus is not prcd.

Genetic markers of the present invention can be made using different methodologies known to those in the art. For example, using the map illustrated in FIG. 1, the prcd-informative region of canine chromosome 9 may be microdissected, and fragments cloned into vectors to isolate DNA segments which can be tested for linkage with the prcd gene locus. Alternatively, with the nucleotide sequences provided in Table 1, isolated DNA segments can be obtained from the prcd-informative region of canine chromosome 9 by nucleic acid amplification (e.g., polymerase chain reaction) or by nucleotide sequencing of the relevant region of chromosome 9 ("chromosome walking"). Using the linkage test of the present invention, the DNA segments may be assessed for their ability to co-segregate with the prcd gene locus (e.g., a LOD score may be calculated), and thus determine the usefulness of each DNA segment in a molecular diagnostic assay for detection of prcd or the carrier status.

The diagnostic method of the present invention may be used to determine the prcd locus genotype of an individual dog, or a set of dogs that are closely related to a dog known to be affected with prcd, by identifying in each of these dogs which alleles are present using a set of marker loci linked to prcd. These linked marker loci cover a region ("prcd-informative region") commencing approximately 37.5 centimorgans on one side of the prcd locus (FIG. 1, "*") and extends beyond the prcd locus to the proximal end of chromosome 9 (FIG. 1, "**") Linked marker loci that are located downstream and in close proximity to the prcd locus include microsatellite markers 2263 and 173, and canine genes APOH (apolipoprotein) and MLC1 (myosin light chain 1; locus name MYL4), RARA (retinoic receptor α), and distant gene NF1 (neurofibromin) as summarized in Table 1. Linked marker loci that are located proximally (e.g., upstream) and in close proximity to the prcd locus include canine genes GRB2 (encoding a protein involved in signal transduction), GALK (galactokinase 1), and TK1 (thymidine kinase 1) as summarized in Table 1.

TABLE 1

| marker | approx. size of amplified product | sequence of primers | linkage to prcd locus: Zmax at θ |
| --- | --- | --- | --- |
| ms 173 | 110 bp ± 2n bp | SEQ ID NOs: 1 & 2 | 13.7 at 3.4 cM |
| ms 474 | 107 bp ± 2n bp | SEQ ID NOs: 3 & 4 | 2.8 at 22.5 cM |
| ms 250 | 114 bp ± 2n bp | SEQ ID NOs: 5 & 6 | 3.2 at 16.7 cM |
| ms 2263 | 213 bp ± 4n bp | SEQ ID NOs: 7 & 8 | 12.3 at 4.9 cM |
| APOH | 430 or 434 bp | SEQ ID NOs: 9 & 10 | 8.3 at 5.1 cM |
|  | 347 bp | SEQ ID NOs: 11 & 12 | 8.3 at 5.1 cM |
|  | 158 bp | SEQ ID NOs: 13 & 21 | 8.3 at 5.1 cM |
| MLC1 | 1.5 kb | SEQ ID NQs: 14 & 15 | 16.0 at 4.2 cM |
| GRB2 | 1.5 kb | SEQ ID NOs: 16 & 17 | 11.7 at 0 cM |

TABLE 1-continued

| marker | approx. size of amplified product | sequence of primers | linkage to prcd locus: Zmax at θ |
|---|---|---|---|
| RDM | 1.5 to 1.6 kb | SEQ ID NOs: 18 & 19 | 3.8 at 11.5 cM |
|  | 1.2 to 1.3 kb | SEQ ID NOs: 18 & 20 | 3.8 at 11.5 cM |
|  | 253 bp and 354 bp | SEQ ID NOs: 30 & 31 | 5.0 at 9.7 cM |
| TK1 | 121 bp ± 2n bp | SEQ ID NOs: 22 & 23 | 13.5 at 1.9 cM |
| GALK1 | 184 bp ± 2n bp | SEQ ID NOs: 24 & 25 | 4.2 at 0.0 cM |
| RARA | 128 bp ± 2n bp | SEQ ID NOs: 26 & 27 | 7.6 at 11.5 cM |
| NF1 | 302 bp ± 2n bp | SEQ ID NOs: 28 & 29 | .3* at 11.5 cM |

*The low value (Zmax) for linkage to prcd is an effect of the distance from the prcd gene locus. NF1 is included based on its strong linkage (Zmax 6.27 at 3.7 cM) to prcd-linked markers 474 and 250.

In Table 1, given is the approximate size of the amplified product resulting from amplification using the respective primer pair. It will be appreciated by those skilled in the art that the alleles that make up the genotypes of the genetic markers in the canine population (or within a specific breed of dog, or within a specific family of dogs) may vary by a single base pair or limited number of base pair substitutions in the DNA, or the differences may comprise many base pairs as seen in a transversion. Thus, polymorphisms for the alleles may also show variation in size from the approximate size illustrated above. Nevertheless, analysis of a pedigree with the genetic marker using the methods according to the present invention may be sufficient to establish that the genetic marker may be used for that pedigree in detecting a mutation in the prcd gene locus.

EXAMPLE 1

This embodiment illustrates the localization of the prcd gene locus to canine chromosome 9. Additionally, this embodiment describes the identification of other markers linked to the prcd gene locus, and thus the characterization of the prcd-informative region of chromosome 9.

To find the chromosomal location of the prcd gene locus, a linkage of a microsatellite marker was established by analyzing the polymorphic alleles of the marker to prcd pedigrees. Pedigrees informative of prcd, as well as pedigrees not informative of prcd, were developed to assist in the identification of prcd linked marker loci. Linkage of a microsatellite marker to the prcd locus was established by analyzing the polymorphic alleles of the marker to the prcd pedigrees. Canine-rodent hybrid cell lines were constructed by fusing canine fibroblasts with rodent A9 cells (cell lines publically available from Coriell Institute, Camden, N.J.). Using primers for each linked microsatellite marker, 200 ng of genomic DNA from each hybrid cell line was analyzed by nucleic acid amplification using methods previously described (Ostrander et al., 1993, *Genomics* 16:207–213; 1995, *Mamm. Genome* 6:192–195; Franciso et al., 1996, *Mamm. Genome* 7:359–362). A microsatellite marker (ms 173, or Cxx173) was identified in each of the 3 different rodent-canine hybrid cell lines. Using sets of primers specific for other microsatellite markers, and using similar techniques, it was found that the cell lines were associated with a few other microsatellite markers. Linkage of the microsatellite markers to the prcd locus was established by analyzing the polymorphic alleles of each marker to the prcd pedigree. This genotyping resulted in the determination that three other microsatellite markers (250, 474, and 2263; see Table 1) were found to be associated with the prcd locus. One cell line in which all 4 microsatellite markers (ms 173, ms 474, ms 250, and ms 2263) were located, was also found to contain the BRCA1 gene. Since the BRCA1 gene is found on human chromosome 17q, this (and subsequent mapping experiments) established that the cell line contains the canine analogue of human chromosome 17.

Using this information, the canine chromosome analogs of other genes located on human chromosome 17q were partially characterized. Polymorphisms in the canine genes identified were detected by RFLP, as described in more detail herein. Additionally, polymorphisms associated with the canine genes were identified by microsatellite analysis. Briefly, primer pairs for each microsatellite was used in a nucleic acid amplification reaction containing genomic DNA. One of the primers had been previously radiolabeled with $^{32}$P-ATP. Following nucleic acid amplification, the amplified products were analyzed by polyacrylamide gel electrophoresis with subsequent autoradiography. Polymorphic markers associated with the canine genes were used to establish linkage to the prcd gene locus by analyzing the markers in pedigrees informative of prcd using techniques already described herein.

Several genes have been linked to the prcd locus. The canine apolipoprotein H (APOH) cDNA sequence is listed in a gene database (Genebank accession #X72933). For example, using the methods described in Example 2 herein, primers from this gene were used to screen canine genomic DNA for polymorphisms. Briefly, nucleic acid amplification was performed, the amplified products were digested with the restriction enzyme specified, and the digested products were electrophoresed in 6% polyacrylamide gels and stained with ethidium bromide for visual analysis. Three polymorphisms were identified in the canine APOH gene. All polymorphisms are located in a single intron (of ~1.4 kb). The first polymorphism is the insertion of tetranucleotide TGAC. As illustrated in Table 1, using as primers SEQ ID NOs: 9 & 10, a 430 to 434 bp product is amplified from canine genomic DNA by polymerase chain reaction (e.g., with 1.5 mM MgCl$_2$ for 40 cycles at 94° C. for 30 seconds; 59° C. for 30 seconds; and 72° C. for 40 seconds). Digestion of this product with restriction enzyme BsmAI produced a polymorphic 100 bp fragment or 96 bp fragment, in addition to other nonpolymorphic DNA fragments. When both alleles are present in a sample, 2 extra bands are detected due to the presence of two different heteroduplexes.

The second polymorphism is a single nucleotide polymorphism caused by the insertion or deletion of the nucleotide A. The sequence variation does not cause an RFLP. As illustrated in Table 1, using as primers SEQ ID NOs: 11 & 12, a 347 bp product is amplified from canine genomic DNA by polymerase chain reaction (e.g., with 1.5 MM MgCl$_2$ for 40 cycles at 94° C. for 30 seconds; 60° C. for 30 seconds; and 72° C. for 60 seconds). Presence of both alleles would give 2 bands: a lower band corresponding to a homoduplex for each allele (indistinguishable in a 6% polyacrylamide gel), and an upper band corresponding to the heteroduplex formed between the two alleles.

The third polymorphism is a single nucleotide (G/A) polymorphism. This sequence variation does not change any particular restriction enzyme site. As illustrated in Table 1, using as primers SEQ ID NOs: 13 & 21, a 158 bp product is amplified from canine genomic DNA by polymerase chain reaction (e.g., with 1.5 mM MgCl$_2$ for 40 cycles at 94° C. for 30 seconds; 58° C. for 30 seconds; and 72° C. for 60 seconds). For easy identification of the alleles, a restriction site for restriction enzyme AciI was created by a mismatch primer (SEQ ID NO:13) in which a base in the original sequence was changed from a T to a G. Thus, when the polymorphic site contained a G (not an A), the AciI site was created. Digestion of this product with restriction enzyme AciI cleaves the 158 bp fragment to 133 bp and 25 bp fragments when the polymorphic site contained a G.

Another gene linked to the prcd locus is the atrial myosin light chain 1 gene (MLC1; locus name—"MYL4") which maps to 17qter of human chromosome 17. Primers from conserved regions of this gene were used to screen canine genomic DNA for poly-morphisms. Two polymorphisms were identified in the canine MLC1 gene. The first polymorphism is a BstN I restriction fragment length polymorphism (RFLP). As illustrated in Table 1, using as primers SEQ ID NOs: 14 & 15, a 1.5 kb product is amplified from canine genomic DNA by polymerase chain reaction (e.g., with 2.5 mM $MgCl_2$ for 40 cycles at 94° C. for 30 seconds; 65° C. for 60 seconds; and 72° C. for 120 seconds). Digestion of this product with restriction enzyme BstN I produced six non-polymorphic fragments, and one polymorphic fragment of approximately 140 bp. When the polymorphic site is present (allele 2), the 140 bp fragment is digested to fragments of approximately 120 bp and 20 bp. Absence of polymorphic site is allele 1.

The second polymorphism is a BsrI RFLP. The 1.5 kb product, amplified using primers SEQ ID NOs: 14 & 15, and digested with BsrI, generates two non-polymorphic fragments, and one polymorphic fragment of approximately 340 bp. Presence of the Bsr I polymorphic site (allele 4) cleaves the 340 bp fragment to fragments of approximately 250 bp and 90 bp. Absence of poly-morphic site is allele 3.

Another gene linked to the prcd locus is the GRB2 gene which maps to human 17q24-q25 and mouse chromosome 11 (between the APOH and TK1 genes). Primers from conserved regions of this gene were used to screen canine genomic DNA for polymorphisms. Two polymorphisms, a base pair mismatch in 2 different fragments, were identified in the canine GRB2 gene. As illustrated in Table 1, using as primers SEQ ID NOs: 16 & 17, a 1.5 kb product is amplified from canine genomic DNA by polymerase chain reaction (e.g., with 2 mM $MgCl_2$ for 40 cycles at 94° C. for 30 seconds; 65° C. for 60 seconds; and 72° C. for 120 seconds). Digestion of this product with restriction enzyme Hinf I produces several non-polymorphic fragments, and two polymorphic fragments (320 bp and 420 bp). Allelic difference in the pedigree samples were determined based on the presence of homoduplex and heteroduplex in the digest.

Another gene linked to the prcd locus is the thymidine kinase 1 gene (TK1) which maps to the opposite side (see FIG. 1) of the prcd gene locus when compared to most markers listed in Table 1. Primers for microsatellite sequences physically associated with the TK-1 gene were used to screen canine genomic DNA for polymorphisms (Werner et al. 1997, Genomics, 42:74–82). The marker contains a polymorphic dinucleotide repeat: $(TG)_2(TC)_n$. As illustrated in Table 1, using as primers SEQ ID NOs: 22 & 23, a 123 bp product and other variants are amplified from canine genomic DNA by polymerase chain reaction.

Another gene linked to the prcd locus is the galactokinase 1 gene (GALK1) gene. Primers for microsatellite sequences physically associated with the GALK-1 gene were used to screen canine genomic DNA for polymorphisms. The marker contains a polymorphic dinucleotide repeat: $(CA)_n$. As illustrated in Table 1, using as primers SEQ ID NOs: 24 & 25, a 186 bp product and other variants are amplified from canine genomic DNA by polymerase chain reaction.

Another gene linked to the prcd locus is the retinoic acid receptor gene α (RARA) gene. Primers for microsatellite sequences physically associated with the RARA gene were used to screen canine genomic DNA for polymorphisms. The marker contains a polymorphic dinucleotide repeat: $(CA)_n$. As illustrated in Table 1, using as primers SEQ ID NOs: 26 & 27, a 130 bp product and other variants are amplified from canine genomic DNA by polymerase chain reaction.

Another gene linked to the prcd locus is the neurofibromin gene (NF1) gene. As noted above, the low value (Zmax) for linkage to prcd is an effect of the distance from the prcd gene locus. NF1 is included based on its strong linkage (Zmax 6.27 at 3.7 cM) to prcd-linked markers 474 and 250. Primers for microsatellite sequences physically associated with the NF1 gene were used to screen canine genomic DNA for polymorphisms (Werner et al. 1997, Genomics, 42:74–82). The marker contains a polymorphic dinucleotide repeat: $(CA)_n$. As illustrated in Table 1, using as primers SEQ ID NOs: 28 & 29, a 304 bp product and other variants are amplified from canine genomic DNA by polymerase chain reaction.

Random amplified polymorphic DNA (RAPD) markers are useful for identifying inter-species or intra-species differences in animal genomes where little information is available about the genome. RAPD is a nucleic acid amplification (e.g., polymerase chain reaction)-based technique that depends on single primer binding, in the appropriate opposing directions, to essentially identical paired sequences which can be located on opposite strands and within a hundred to a thousand or so base pairs of each other. Methods of RAPD analysis for genetic analysis of domestic animals have been described in the art (Cushwa and Medrano, 1996, Animal Biotechnology 7:11–31).

Illustrated herein is the identification of a RAPD marker linked to the prcd locus. Genomic DNA was isolated from dogs belonging to prcd-informative pedigrees. A series of polymerase chain reactions were performed in screening single primers of 10 nucleotides each under low stringency conditions (e.g., with 2 mM $MgCl_2$ for 40 cycles at 94° C. for 60 seconds (5 minutes for first cycle); 37° C. for 120 seconds; and 72° C. for 120 seconds for 39 cycles with an additional extension time 6 minutes after the last cycle). Amplification products were analyzed by agarose gel electrophoresis to identify polymorphisms between pairs of informative parents in the pedigrees. From the initial screening of 400 commercially available primers, a single primer (the first 10 nucleotides of SEQ ID NOs:18 & 19, see also Table 1) was found to amplify a fragment only from normal dogs, as compared to prcd-affected dogs. The amplified polymorphic DNA product was cloned and sequenced. Specific primers (SEQ ID NOs:18 & 19) were designed based on the sequence data, and then used in nucleic acid amplification reactions to characterize the genotype of those dogs informative for both the rapid-derived marker (RDM) and the prcd disease locus. Nucleic acid amplification using SEQ ID NO:18 and SEQ ID NO:19 resulted in a 1.6 kb (allele 1) amplified product and a 1.5 kb (allele 2) amplified product. Using a primer pair comprising an internal primer (SEQ ID NO:20) and SEQ ID NO:18, the size of the amplified polymorphic products obtained by nucleic acid amplification were reduced to 1.2 kb and 1.3 kb. The difference between allele 1 and allele 2 was due to insertion of 101 nucleotides in the longer allele. This stretch of 101 nucleotides contains a poly A stretch of 30 nucleotides at the 3'-end. Another pair of primers (SEQ ID NOs. 30 and 31) were designed to amplify smaller fragments (253 bp and 354 bp; see Table 1) containing the variable sequence between the 2 alleles for ease of identification. Amplification was performed at 40 cycles of 94° C. for 30 seconds (2 minutes for first cycle); 61° C. for 30 seconds; and 72° C. for 60 seconds with an additional extension time 8 minutes after the last cycle. Amplification products were analyzed by 2% agarose gel electrophoresis. Screening 5 pedigrees with these primer pairs identified 3 obligate recombinants among 31 informative offspring.

With the knowledge demonstrated herein that DNA sequences (polymorphic markers) of canine chromosome 9 have been identified as being linked to the prcd locus, additional markers may be generated from the known sequences or indicated location on canine chromosome 9, for use in the method of the present invention. This is because the strong homology of canine chromosome 9 in the prcd-informative region to corresponding regions of human chromosome 17 and mouse chromosome 11 indicate that any gene or expressed tag sequence that is mapped to these analogous regions in the human or mouse may also map to the prcd-informative region of canine chromosome 9. Thus, genes or conserved sequences that map on human chromosome 17q, between 17q21 and qter, may be analyzed for linkage to the prcd gene locus using the routine methods described herein. Genes that are known to those skilled in the art to map on human chromosome 17q, between 17q21 and qter, include, but are not limited to the genes listed in Table 2. For example, using the known sequence of any gene identified in Table 2, the corresponding region of the canine genomic DNA from both prcd-affected and normal dogs can be identified to either determine the sequence of both products or digest both products with restriction enzymes, to find polymorphic differences either at the sequence level or in the restriction enzyme digest pattern (respectively) of two products. Once such a polymorphic difference is found, further characterization of the polymorphic sequence will yield a marker linked to the prcd gene locus. As illustrated herein, this same technique has resulted in identification of APOH (17q23-qter), MLC1 (17q21-qter), and GRB2 (17q24-q25) as genetic markers linked to the prcd gene locus, and thus useful in the diagnostic method of the present invention.

TABLE 2

| Name (known abbreviation) | Cytogenic location in humans | Accession number, GDB |
|---|---|---|
| ICAM2 | 17q23–q25 | 118816 |
| TOP2A | 17q21–q22 | 118884 |
| A12M4 | 17q21–q22 | 118953 |
| COL1A1 | 17q21.3–q22 | 119061 |
| CSH1 | 17q22–q24 | 119084 |
| CSHL1 | 17q22–q24 | 119085 |
| MIC6 | 17q21–qter | 119391 |
| MSK18 | 17q22–q23 | 119406 |
| FDXR | 17q24–q25 | 119659 |
| ALDOC | 17pter–qter | 119670 |
| CSH2 | 17q22–q24 | 119813 |
| DCP1 | 17q23 | 119840 |
| GAA | 17q23 | 119965 |
| GH1 | 17q22–q24 | 119982 |
| GH2 | 17q22–q24 | 119983 |
| GIP | 17q22–q24 | 119985 |
| WNT3 | 17q21–q22 | 120104 |
| KRT15 | 17q21–q23 | 120124 |
| KRT19 | 17q21–q23 | 120131 |
| MPO | 17q21.3–q23 | 120192 |
| NGFR | 17q21–q22 | 120234 |
| PRKAR1 | 17q23–q24 | 120313 |
| UMPH2 | 17q23–q25 | 120480 |
| HOXB@ | 17q21–q22 | 120657 |
| HCXB5 | 17q21–q22 | 120659 |
| HOXB6 | 17q21–q22 | 120660 |
| HOXB7 | 17q21–q22 | 120660 |

TABLE 2-continued

| Name (known abbreviation) | Cytogenic location in humans | Accession number, GDB |
|---|---|---|
| HOXB8 | 17q21–q22 | 120661 |
| HOXB9 | 17q21–q22 | 120662 |
| HOXB4 | 17q21–q22 | 120663 |
| HOXB3 | 17q21–q22 | 120664 |
| HCXB2 | 17q21–q22 | 120665 |
| HOXB1 | 17q21–q22 | 120666 |
| KRT13 | 17q21–q23 | 120740 |
| DDX5 | 17q24–qter | 120747 |
| BCL5 | 17q22 | 125178 |
| SCN4A | 17q23.1–q25.3 | 125181 |
| ATP6N1 | 17q21–qter | 125314 |
| PTMS | 17q12–q22 | 125555 |
| CLTC | 17q11–qter | 125862 |
| TNFAIP1 | 17q22–q23 | 127514 |
| NM23 | 17q21–q22 | 127965 |
| PRKCA | 17q22–q24 | 128015 |
| NM23-H2 | 17q21–q22 | 128028 |
| ITGB4 | 17q11–qter | 128028 |
| HYKPP | 17q22–q24 | 128190 |
| HLF | 17q22 | 131402 |
| CA4 | 17q23 | 131660 |
| CACNLB1 | 17q21–q22 | 132012 |
| CACNLG | 17q24 | 132015 |
| IGB | 17q23 | 133786 |
| SSTR2 | 17q24 | 134186 |
| SOX9 | 17q24.3–q25.1 | 134730 |
| CYB561 | 17q11–qter | 228138 |
| ZNF147 | 17q21.3–q22 | 282672 |
| ACOX | 17q24–q25 | 282672 |
| TCF11 | 17q22 | 316220 |
| ACLY | 17q21–q22 | 316220 |
| RCH1 | 17q23.1–q23.3 | 374081 |
| COIL-PEN | 17q22–q23 | 435364 |
| DDPAC | 17q21–q22 | 454774 |
| RP17 | 17q22–q24 | 683199 |
| NOS2B | 17p13.1–q25 | 547926 |
| NOS2C | 17q13.1–q25 | 547943 |
| PRPSAP1 | 17q24–q25 | 567139 |
| SYM1 | 17q21–q22 | 512174 | full names and sequences available in the Genome Database

EXAMPLE 2

This embodiment illustrates the determination of the prcd locus genotype of a set of dogs that are closely related to a dog known to be affected with prcd, using a single linked marker. This embodiment of the diagnostic method of the present invention depends on first identifying the allele(s) present, at one or more marker loci linked to prcd, in the affected dog. This establishes the "phase" for determining whether in this pedigree any or all of the marker loci are informative for detecting a mutation in the prcd gene locus. Two or more alleles (one per locus) are said to be in phase if they are on the same chromosome. Alleles on the same chromosome are in "coupling phase"; whereas two alleles (at different loci) that lie on opposite chromosomes are in "repulsion". For example, if a dog affected with prcd has two copies of an allele which is identified by any one of the linked marker loci, then this allele is in phase (coupling phase) with the mutant allele at the prcd locus. If a nonaffected close relative of this affected dog has one or both alleles at any one of the linked marker loci which is different from the allele(s) present in the affected dog, then this marker locus is said to be informative in this pedigree.

Once the phase, and the informative value, have been established at one or more of the prcd linked marker loci, the prcd genotype of close relatives of the dog may be determined by evaluating their genotype using these phase, informative marker loci. In different pedigrees, one skilled in the art will appreciate that different markers and combinations of markers may be more useful, depending on whether the affected dog has different alleles at the marker loci from nonaffected relatives. Further, as provided herein, using the teachings of the present invention new markers may be identified for use in pedigrees in which none of above-listed markers show diagnostic utility. However, a strength of the diagnostic method according to the present invention is that the number of polymorphic loci already identified essentially makes it improbable that the test will be non-diagnostic in any given pedigree.

For any one marker, the probability that a tested dog will receive from a parent the same prcd allele that was in phase with the marker allele in the parent, is a function of the linkage distance between the marker locus and the prcd locus.

For example, as compared to some of the other markers illustrated in FIG. 1 and Table 1, ms 474 ("Cxx474" in FIG. 1) is approximately 20 centimorgans from the prcd gene locus. This means that approximately 80% of the offspring will receive from a parent the prcd allele and the ms 474 locus allele that were in phase (on the same chromosome) in that parent. Conversely, approximately 20% of the offspring will receive the prcd allele and the ms 474 locus allele that were on the opposite chromosome arm of that parent. In contrast, marker GRB2 is only 0 to 1.5 centimorgans from the prcd gene locus. Such close linkage means that the prcd allele and the GRB2 locus allele will be transmitted in phase in over 95% of reproductive events (meioses). With only one marker, analyses are based on the probability of whether the 2 loci (marker and prcd) were passed from a parent to offspring maintaining this phase relationship; or if the phase relationship was altered, e.g., via a recombination event. Using one marker, one is not able to distinguish a genotype representing a phase-preserved chromosome from a genotype representing a recombination event. However, if a closely linked marker (e.g., GRB2, or GALK1, or TK1) is used for genotype analysis, and if one assumes that all pups receive the prcd allele in phase, the likelihood of error in such analysis is less than 5%. Because such markers are extremely closely linked to the prcd gene locus, any one of these markers alone is sufficient to establish the prcd genotype for individuals in a pedigree. Thus, in one embodiment of the present invention, a single marker (preferably a marker in a distance range of 0 to 1.5 centimorgans from the prcd gene locus) located in the prcd-informative region may be used to determine of the prcd locus genotype of a set of dogs that are closely related to a dog known to be affected with prcd.

Using the method of the present invention, tested is a single individual or tested are multiple individuals in a pedigree in which one or more known and available near relatives are affected with prcd. In this situation, determined is whether the individuals tested are homozygous normal (wildtype; +/+); heterozygous or carrier (prcd/+); or homozygous prcd affected (prcd/prcd) at the prcd gene locus. In order to make this determination, it is necessary to type both the known affected dog(s) and the dogs to be tested at at least one (and usually several) of the genetic markers in the prcd-informative region of chromosome 9.

Genotyping is based on the analysis of genomic DNA which is extracted using standard methods known to those skilled in the art, such as using a lysing buffer (e.g., 10 mM Tris pH 8.3, 50 mM KCl, 1.5 mM $MgCl_2$, 0.01% gelatin, 0.45% NP40™, 0.045% Tween 20™, and 60 µg/ml proteinase K) to lyse cells containing the DNA. DNA is extracted from specimens which may include blood (e.g., fresh or frozen), tissue samples (e.g., spleen, buccal smears), and hair samples containing follicular cells. Once the genomic DNA is isolated and purified, nucleic acid amplification (e.g., polymerase chain reaction) is used to amplify the region of DNA corresponding to each genetic marker to be used in the analysis. While conditions may vary slightly depending on the primer sequences used, generally nucleic acid amplification is performed for 30–40 cycles in a volume of 25 µl containing reaction buffer (e.g., 50 mM KCl, 10 mM Tris-HCl, pH 8.3, 1.0 to 3.0 mM $MgCl_2$); 0.13 each dNTPs (DATP, dCTP, dGTP, and dTTP); 0.2 µM oligonucleotide primer; 10 ng template DNA; and 0.5 units of thermostable DNA polymerase.

A diagnostic kit for the method in this embodiment comprises, in separate packaging, at least one oligonucleotide selected from the group consisting of SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:30, SEQ ID NO:31, and a combination thereof; and may further comprise at least one additional reagent selected from the group consisting of a lysing buffer for lysing cells contained in the specimen; enzyme amplification reaction components dNTPs, reaction buffer, and amplifying enzyme; and a combination of the additional reagents.

EXAMPLE 3

This embodiment illustrates the determination of the prcd locus genotype of a single dog, or from a set of dogs that are closely related to a dog known to be affected with prcd, using more than one linked marker (a combination of linked markers) found in the prcd-informative region. This embodiment of the diagnostic method of the present invention has several advantages over using a single linked marker in genotype analysis. For example, a number of mutations in the prcd gene may cause the prcd disease phenotype; and the nature of the mutation may vary amongst pedigrees and amongst affected breeds. Using multiple linked markers may detect more than one mutation, making the method more informative than a single marker-based method for determination of the prcd locus genotype.

Additionally, two or more marker loci which are shown to be informative can markedly increase the accuracy of the test by reducing the risk of error. The reduction in risk is partly due to the fact that the likelihood of two recombinations occurring in the same region is, generally speaking, the product of the combined probabilities for each recombination separately. Thus, even for distances moderately greater than 1.5 centimorgans from the prcd gene locus, this combined probability yields very low error rates. Using multiple markers, all of the informative markers may be located on the same side (e.g., non flanking) of the prcd gene locus. In a preferred embodiment of using multiple markers, at least one marker is proximal (towards the centromeric end of chromosome 9) to the prcd gene locus (e.g., GRB2, or TK1), and at least one marker is located distal (e.g., APOH) so that at least one marker flanks either side of the prcd gene locus.

Multiple non flanking informative markers (e.g., clustered on one side of the prcd gene on chromosome 9) may provide additional information concerning recombination events occurring between the markers. For example, if no recombination event took place between RDM and the APOH marker, then the likelihood of a recombination event between the APOH group and the prcd gene locus is simply related to the recombination distance between the APOH marker (and marker cluster MYL4, ms 2263, and ms 173; See FIG. 1) to the prcd locus. In continuing this example, if a recombination event is detected between RDM marker and the APOH marker, the likelihood is much greater that the prcd gene locus was transmitted in phase with the nearest marker (in this case, APOH). Thus, even though the recombination distance from the APOH marker to the prcd gene locus is approximately 5 centimorgans, the probability of a recombination between APOH and prcd, given a detected a recombination event in the flanking region, is less than 5%.

Multiple flanking informative markers (e.g., wherein there is at least one marker located on either side of the prcd gene on chromosome 9) may provide additional information, including an accurate determination of prcd-affected or non-affected status, depending on the informativeness of the markers used and their distance from the prcd-gene locus. For example, using APOH (or other marker in the same cluster as illustrated in FIG. 1) as an informative marker and using GRB2 as an informative marker, all dogs can be scored as either nonrecombinant or recombinant in the flanking region (defined by APOH at one end, GRB2 at the other end, and the prcd gene locus located therebetween). For all dogs displaying no recombination in this flanking region, the genotype can be assigned with 100% accuracy; i.e. the dogs received the prcd allele that was in phase with the same flanking region of the parent. This situation would be expected in approximately 92.5% of dogs.

For dogs displaying a recombination event in the flanking region (expected in the remaining approximately 7.5%), a relative probability can be given as to whether the recombination event took place between APOH and the prcd allele versus between the prcd allele and the GRB2 marker. Since recombination is approximately 3 times more likely for the former than the latter, a dog displaying a recombinant event in the flanking region has a 75% probability of receiving the prcd allele in phase with GRB2, and a 25% probability of receiving the prcd allele in phase with APOH from the parent.

Tables 1 and 3 provide evidence that the linkage of the markers of the present invention to the prcd locus is statistical; i.e., that the pattern is one of cosegregation of the marker with the disease locus, rather than a segregation pattern occurring by chance. It was necessary to examine several informative pedigrees to demonstrate the linkage, and for statistical analyses to be performed. Table 3 summarizes a number of prcd informative pedigrees, including the number of dogs sampled to establish linkage for the different polymorphisms, and LOD score determinations for the markers identified in Table 1.

TABLE 3

| Cross | p953x p893 | p703x p893 | p703x p780 | p868x p827 | p848x p827 | p924x p898 | p924x p972 | p924x p831 |
|---|---|---|---|---|---|---|---|---|
| pups | 5 | 3 | 14 | 6 | 5 | 6 | 14 | 9 |
| RDM | + | | | + | + | + | | + |
| APOH | + | + | + | | | + | | + |
| poly1 | | | | | | | | |
| poly2 | | | | + | + | | | |
| poly3 | | | | | | | + | |
| MLC1 BstNI | + | | | + | +/− | + | + | + |
| BsrI | | + | + | | | | | |
| GRB2 | * | * | + | + | + | * | + | * |
| poly 1,2 | | | | | | | | |

*means not tested

To further illustrate this embodiment, and using the methods described in Example 2 herein, haplotype analyses were performed on selected dogs of prcd informative pedigrees in order to establish linkage, and the order of genes and markers in the prcd-informative region of chromosome 9 illustrated in FIG. 1. Similarly performed haplotype analyses can be used to identify and characterize other linked markers in the prcd-informative region which are useful in the diagnostic method of the present invention.

FIGS. 2–6 illustrate the results of only a few of the haplotype analyses performed on selected dogs of prcd informative pedigrees. In each figure, exemplary markers are listed in relation to their position in the prcd-linkage region, and assigned a number for each allele ("0" indicates not tested). The prcd genotype for each allele is identified either as normal (+), or affected (p). Thus, using the method of the present invention, an illustration of the results of genotyping analysis of an individual using exemplary multiple genetic markers may be represented as follows:

| | | |
|---|---|---|
| NF1 | 2 | 2 |
| 250 | 1 | 1 |
| 474 | 3 | 3 |
| RDM | 1 | 1 |
| RARA | 1 | 1 |
| 173 | 2 | 2 |
| APOH | 3 | 3 |
| MLC1 | 2 | 2 |
| 2263 | 5 | 5 |
| prcd | p | p |
| GALK1 | 1 | 1 |
| GRB2 | 1 | 1 |
| TK1 | 1 | 3 |

This dog is known to be prcd-affected, and therefore genotype p/p can be assigned at the prcd gene locus. Because this dog is homozygous at all marker loci except TK1, analysis of any of its closely related descendants will be straight-forward. Any descendants that received a prcd disease allele from this dog will have also received (with high probability) a haplotype consisting of an allele of size 1 at GALK1, an allele of size 1 at GRB2, and an allele of either size 1 or 3 at TK1. With slightly less confidence, one can also expect such a descendant to have received the corresponding alleles (2,3,2,5) at 173, APOH, MLC1, and 2263, respectively. Any immediate offspring of this dog, and this dog's parents, must have one of these two haplotypes (differing only at TK1) in phase with the disease allele the prcd gene locus. In more distantly related dogs, the haplotype including the p allele can change by recombination.

Each of FIGS. 2–6 represents a 3 generation pedigree consisting of grandparents (Note in FIG. 5 a grandparent is shared, thus only 3 grandparents appear); parents in the middle row, and progeny in the lower row. Since prcd is autosomal, the gender of each individual animal has not been specified in the figures. A break in the lining pattern of alleles in a progeny's haplotype represents a recombination event; i.e., the chromosome has portions of both alleles of one of the parents.

Figure 2:
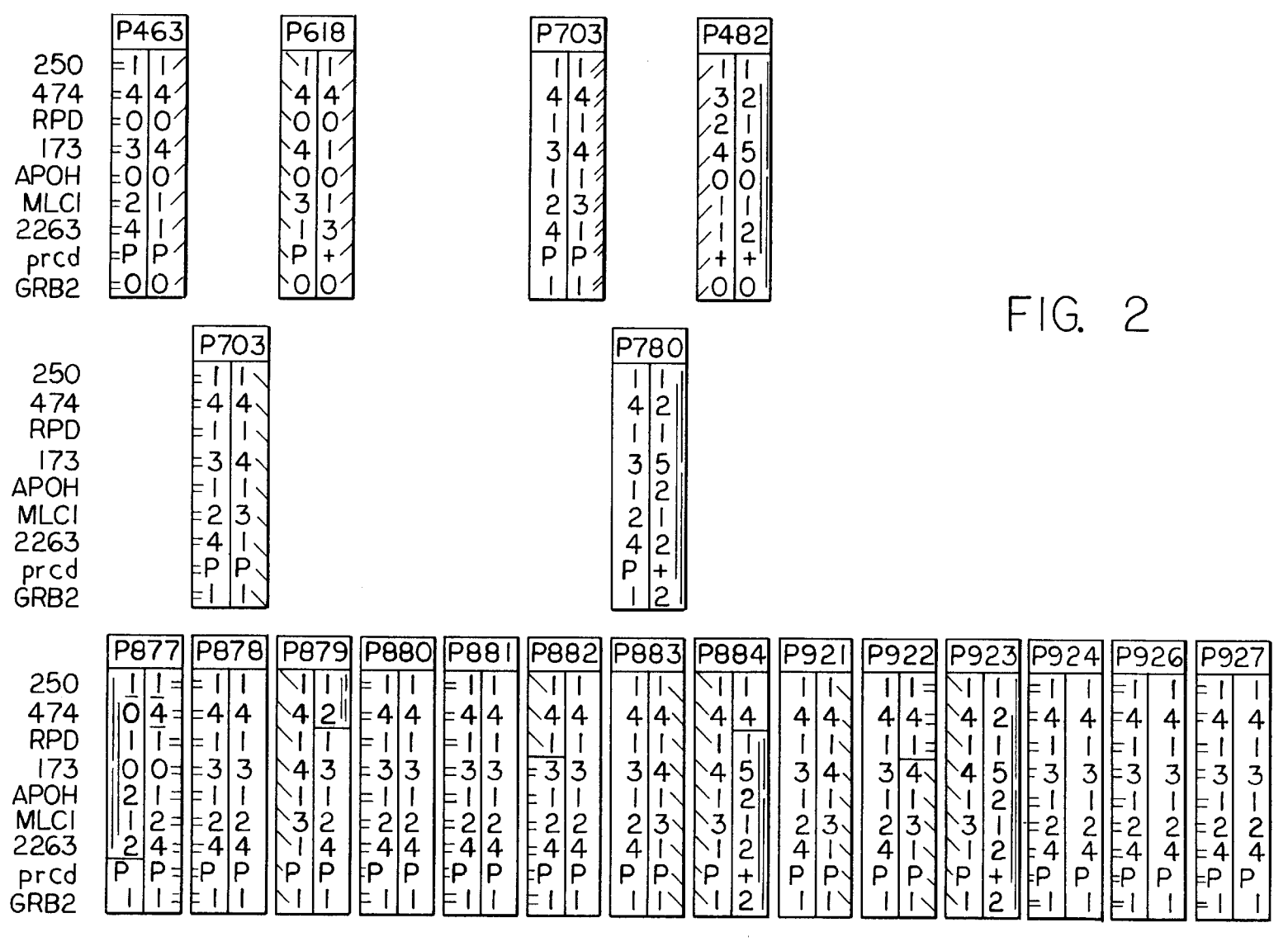
Figure 3:
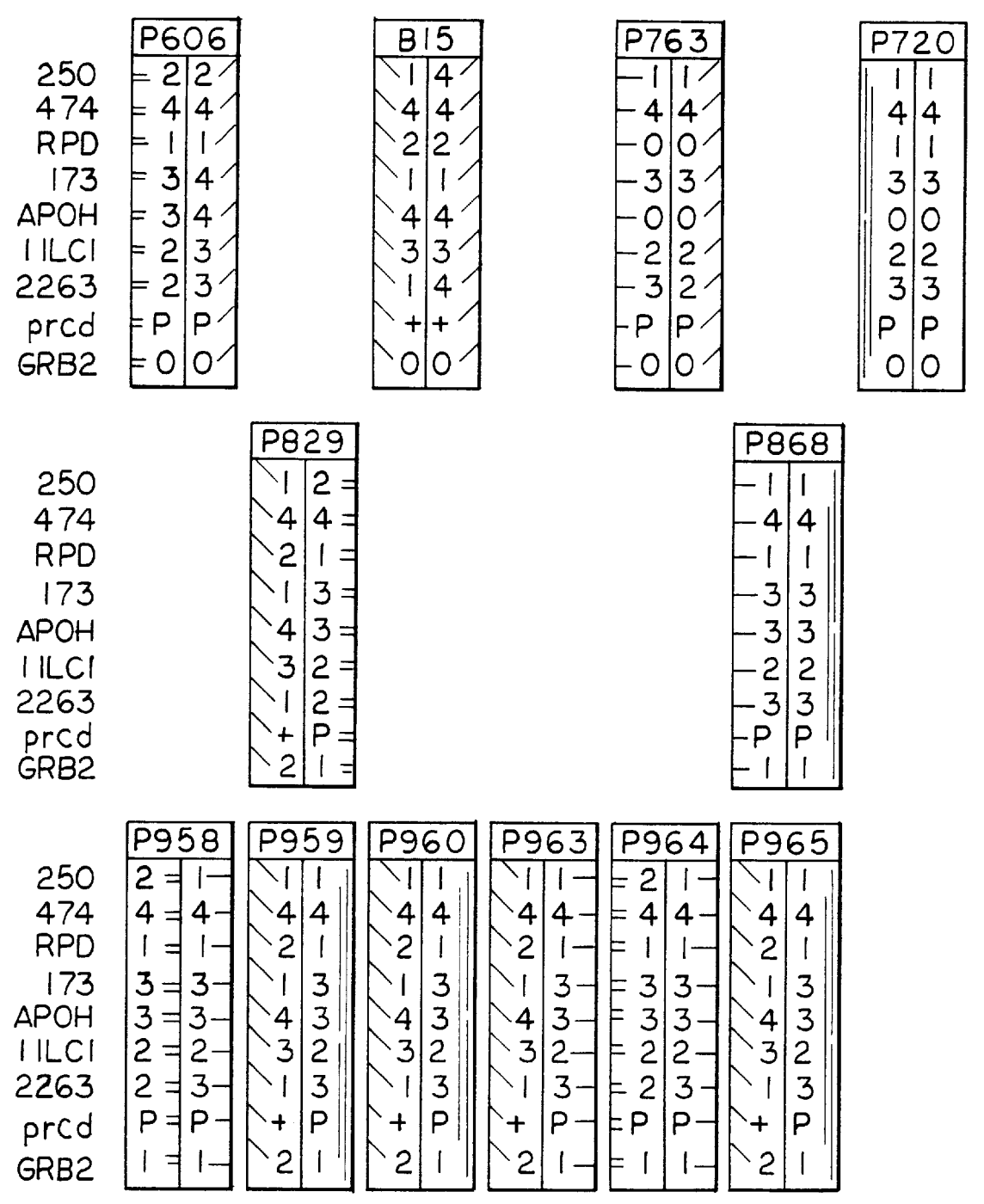
Figure 5:
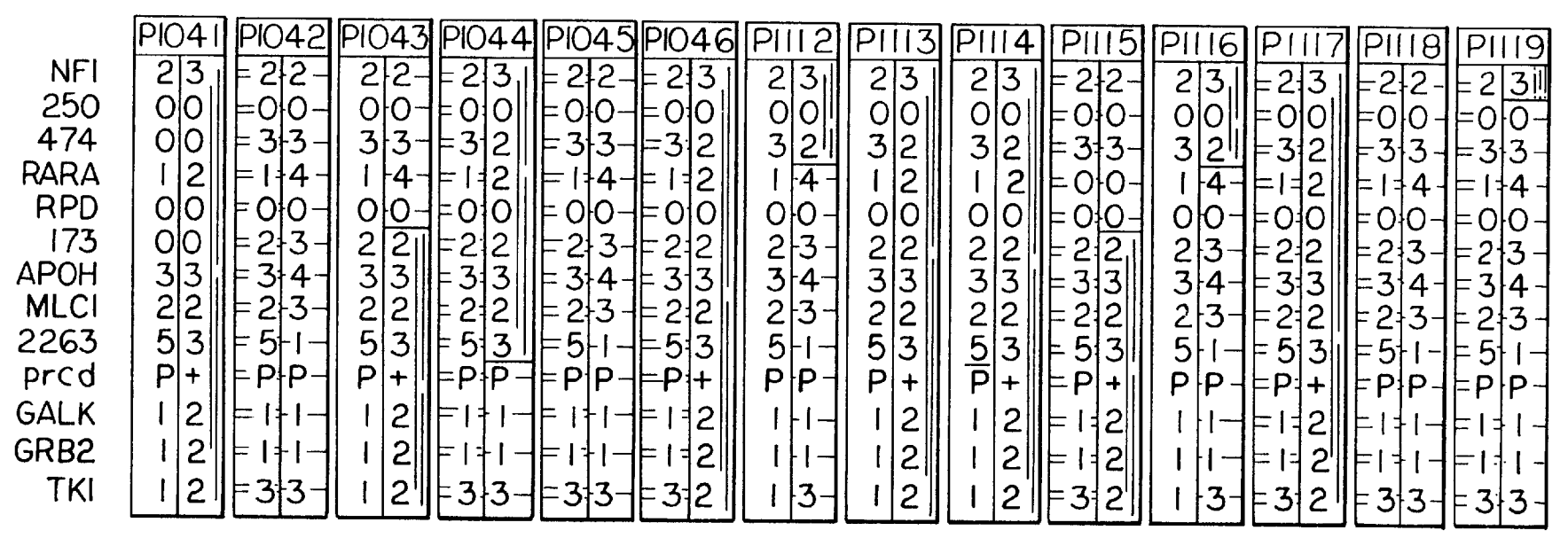
Figure 6:
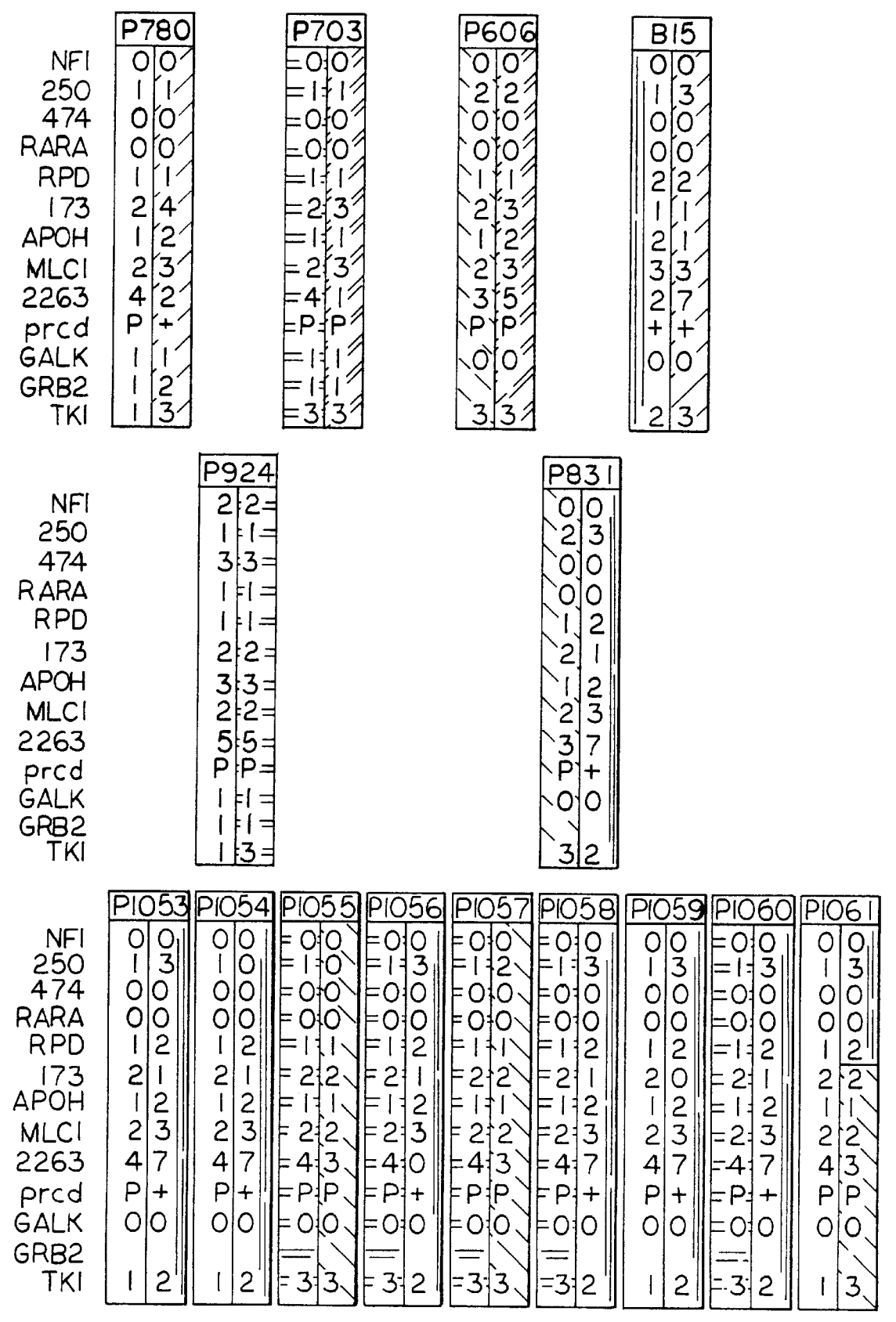

For example, FIG. 2 shows the results of a cross between parents p703 (prcd-affected) with p780 (prcd carrier). Of the 14 progeny (see also Table 3), 12 pups are prcd-affected, whereas 2 pups were determined to be carriers. FIG. 3 shows the results of a cross between parents p827 (prcd-carrier) with p868 (prcd-affected). Of the 6 progeny (see also Table 3), 2 pups are prcd-affected, whereas 4 pups were determined to be carriers. FIG. 4 shows the results of a cross between parents p827 (prcd-carrier) with p848 (prcd-affected). Of the 5 progeny (see also Table 3), 1 pup is prcd-affected, whereas 4 pups were determined to be carriers. FIG. 5 shows the results of a cross between parents p924 (prcd-affected) with p972 (prcd-carrier). Of the 14 progeny (see also Table 3), 7 pups are prcd-affected, whereas 7 pups were determined to be carriers. Note the recombination event in pup p1044, wherein the prcd gene locus co-segregated with closely linked marker GRB2. FIG. 6 shows the results of a cross between parents p924 (prcd-affected) with p831 (prcd-carrier). Of the 9 progeny (see also Table 3), 3 pups are prcd-affected, whereas 6 pups were determined to be carriers.

A diagnostic kit for the method in this embodiment comprises, in separate packaging, a combination of two or more oligonucleotides, wherein the combinations are selected from the group consisting of SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:30, SEQ ID NO:31, and combinations thereof; and may further comprise at least one additional reagent selected from the group consisting of a lysing buffer for lysing cells contained in the specimen; enzyme amplification reaction components dNTPs, reaction buffer, and amplifying enzyme; and a combination of the additional reagents.

EXAMPLE 4

This embodiment illustrates methods by which other markers may be identified in the prcd-informative region of canine chromosome 9. As described in more detail in Example 2 herein, one method for identifying markers linked to the prcd gene locus is to analyze genes or conserved sequences that map on human chromosome 17q, between 17q21 and qter, or homologous regions in other species (preferably mammalian). Using the known sequence of any of such genes or conserved sequences, the corresponding region of the canine genomic DNA from both prcd-affected and normal dogs can be identified. Sequencing of both products or digesting both products with restriction enzymes can be performed to identify polymorphic differences either at the sequence level or in the restriction enzyme digest pattern (respectively) of two products. Once such a polymorphic difference is found, further characterization of the polymorphic sequence will yield a marker linked to the prcd gene locus. The polymorphic sequence may then be used in analyzing individuals in a pedigree informative for both prcd and the newly discovered polymorphism for determining its use in genotyping.

Alternatively, using any of the sequences identified herein as being linked to the prcd gene locus, one skilled in the art can isolate clones containing such sequences from various types of canine DNA libraries using standard techniques known in the art. Such libraries may be commercially available now, or may be custom made for this particular purpose using techniques known in the art (e.g., genomic lambda libraries, cosmid libraries, bacterial artificial chromosome (BAC) libraries, and yeast artificial chromosome (YAC) libraries). The library may be screened using any one or more of the sequences identified herein as a hybridization probe to isolate a genomic clone containing a sequence of interest. Alternatively, using methods known in the art, the hybridization probe (or primer, or primers of a primer pair for amplifying a sequence from a genomic clone) can be an oligonucleotide synthesized from a sequence in the prcd-informative region (e.g., see Table 2). Confirmation that such genomic clone contains sequences which correspond to the prcd-informative region include using the clone to screen the canine rodent cell line which has been demonstrated to contain the prcd-informative region.

Once a clone from such a library has been identified using a prcd-linked probe, the canine genomic DNA insert contained within the clone can be readily screened in any one of several methods known in the art for identifying regions containing sequences that appear to be highly polymorphic. For example, one method comprises digesting the large insert, as obtained from BAC or YAC clones, into smaller fragments with restriction enzymes; packaging the digest products in a plasmid vector; making a small insert $E.$ $coli$ library; plating and rescreening this $E.$ $coli$ library with dinucleotide or tri-nucleotide or tetra-nucleotide microsatellite repeat sequences such as $(CA)_n$, $(CAC)_n$, or $(GAAA)_n$. Positive clones would then be amplified and sequenced to identify the sequences surrounding the microsatellites. Primers derived from these flanking sequences may then be used to amplify the microsatellite from prcd-affected dogs and normal dogs to identify polymorphisms informative for the prcd genotype. Such markers may then be used in the method of the present invention as one of the markers for identifying the prcd gene locus and mutations thereof.

It should be understood that while the invention has been described in detail herein, the examples were for illustrative purposes only. Other modifications of the embodiments of the present invention that are obvious to those of ordinary skill in the art of molecular biology, medical diagnostics, and related disciplines are intended to be within the scope of the appended claims.

What is claimed is:

1. A method for detecting the presence in a canine subject of at least one genetic marker that is genetically linked and co-segregating with a progressive rod-cone degeneration disease trait, wherein the at least one genetic marker consists of a polymorphism that is located in a prcd-informative region on canine chromosome 9, said method comprising analyzing chromosome 9 of the canine subject for the presence of the polymorphism in the prcd-informative region, wherein the presence of the polymorphism is indicative of a genetic marker associated with progressive rod-cone degeneration disease.

2. The method according to claim 1, wherein the at least one genetic marker is selected from the group consisting of microsatellite marker 173, microsatellite marker 474, microsatellite marker 250, microsatellite marker 2263, apolipoprotein H gene, atrial myosin light chain 1 gene, GRB2 gene, thymidine kinase 1 gene, galactokinase 1 gene, retinoic acid receptor α gene, neurofibromin gene, a chromosome 9 RAPD marker located between the atrial myosin light chain 1 gene and the retinoic acid receptor α gene and a combination thereof.

3. The method according to claim 2, wherein the at least one genetic marker is the microsatellite marker 173.

4. The method according to claim 3, wherein the polymorphism is analyzed by using SEQ ID NO:1 and SEQ ID NO:2 as primers in a nucleic acid amplification reaction containing chromosome 9 DNA to obtain an amplified product.

5. The method according to claim 2, wherein the at least one genetic marker is the microsatellite marker 474.

6. The method according to claim 5, wherein the polymorphism is analyzed by using SEQ ID NO:3 and SEQ ID NO:4 as primers in a nucleic acid amplification reaction containing chromosome 9 DNA to obtain an amplified product.

7. The method according to claim 2, wherein the at least one genetic marker is the microsatellite marker 250.

8. The method according to claim 7, wherein the polymorphism is analyzed by using SEQ ID NO:5 and SEQ ID NO:6 as primers in a nucleic acid amplification reaction containing chromosome 9 DNA to obtain an amplified product.

9. The method according to claim 2, wherein the at least one genetic marker is the apolipoprotein H gene.

10. The method according to claim 9, wherein the polymorphism is analyzed by using SEQ ID NO:9 and SEQ ID NO:10 as primers in a nucleic acid amplification reaction containing chromosome 9 DNA to obtain an amplified product, and digesting the amplified product with restriction enzyme BsmAI.

11. The method according to claim 9, wherein the polymorphism is analyzed by using SEQ ID NO:11 and SEQ ID NO:12 as primers in a nucleic acid amplification reaction containing chromosome 9 DNA to obtain an amplified product.

12. The method according to claim 9, wherein the polymorphism is analyzed by using SEQ ID NO:13 and SEQ ID NO:21 as primers in a nucleic acid amplification reaction containing chromosome 9 DNA to obtain an amplified product, and digesting the amplified product with restriction enzyme AciI.

13. The method according to claim 2, wherein the at least one genetic marker is the atrial myosin light chain 1 gene.

14. The method according to claim 13, wherein the polymorphism is analyzed by using SEQ ID NO:14 and SEQ ID NO:15 as primers in a nucleic acid amplification reaction containing chromosome 9 DNA to obtain an amplified product, and digesting the amplified product with restriction enzyme BstNI.

15. The method according to claim 13, wherein the polymorphism is analyzed by using SEQ ID NO:14 and SEQ ID NO:15 as primers in a nucleic acid amplification reaction containing chromosome 9 DNA to obtain an amplified product, and digesting the amplified product with restriction enzyme BsrI.

16. The method according to claim 2, wherein the at least one genetic marker is the GRB2 gene.

17. The method according to claim 16, wherein the polymorphism is analyzed by using SEQ ID NO:16 and SEQ ID NO:17 as primers in a nucleic acid amplification reaction containing chromosome 9 DNA to obtain an amplified product, and digesting the amplified product with restriction enzyme HinfI.

18. The method according to claim 2, wherein the at least one genetic marker is the thymidine kinase 1 gene.

19. The method according to claim 18, wherein the polymorphism is analyzed by using SEQ ID NO:22 and SEQ ID NO:23 as primers in a nucleic acid amplification reaction containing chromosome 9 DNA to obtain an amplified product.

20. The method according to claim 2, wherein the at least one genetic marker is the galactokinase 1 gene.

21. The method according to claim 20, wherein the polymorphism is analyzed by using SEQ ID NO:24 and SEQ ID NO:25 as primers in a nucleic acid amplification reaction containing chromosome 9 DNA to obtain an amplified product.

22. The method according to claim 2, wherein the at least one genetic marker is the retinoic acid receptor α gene.

23. The method according to claim 22, wherein the polymorphism is analyzed by using SEQ ID NO:26 and SEQ ID NO:27 as primers in a nucleic acid amplification reaction containing chromosome 9 DNA to obtain an amplified product.

24. The method according to claim 2, wherein the at least one genetic marker is the neurofibromin gene.

25. The method according to claim 24, wherein the polymorphism is analyzed by using SEQ ID NO:28 and SEQ ID NO:29 as primers in a nucleic acid amplification reaction containing chromosome 9 DNA to obtain an amplified product.

26. The method according to claim 2, wherein the at least one genetic marker is the chromosome 9 RAPD marker located between the atrial myosin light chain 1 gene and the retinoic acid receptor α gene.

27. The method according to claim 26, wherein the polymorphism is analyzed by using SEQ ID NO:18 and SEQ ID NO:19 as primers in a nucleic acid amplification reaction containing chromosome 9 DNA to obtain an amplified product.

28. The method according to claim 26, wherein the polymorphism is analyzed by using SEQ ID NO:18 and SEQ ID NO:20 as primers in a nucleic acid amplification reaction containing chromosome 9 DNA to obtain an amplified product.

29. The method according to claim 26, wherein the polymorphism is analyzed by using SEQ ID NO:30 and SEQ ID NO:31 as primers in a nucleic acid amplification reaction containing chromosome 9 DNA to obtain an amplified product.

30. The method according to claim 1, wherein the at least one genetic marker is a combination of genetic markers.

31. The method according to claim 30, wherein the combination of markers comprises multiple informative markers clustered on one side of a prcd gene on chromosome 9.

32. The method according to claim 30, wherein the combination of markers comprises multiple informative markers, wherein there is at least one marker located on either side of a prcd gene on chromosome 9.

33. The method according to claim 2, wherein the at least one genetic marker is a combination of genetic markers.

34. The method according to claim 33, wherein the combination of markers comprises multiple informative markers clustered on one side of a prcd gene on chromosome 9.

35. The method according to claim 33, wherein the combination of markers comprises multiple informative markers, wherein there is at least one marker located on either side of a prcd gene on chromosome 9.

36. The method according to claim 1, wherein the presence of at least one polymorphism forms a polymorphism pattern, and further comprising comparing the polymorphism pattern observed in the canine subject with a corresponding polymorphism pattern for each parent of the canine subject.

37. The method according to claim 2, wherein the presence of at least one polymorphism forms a polymorphism pattern, and further comprising comparing the polymorphism pattern observed in the canine subject with a corresponding polymorphism pattern for each parent of the canine subject.

38. A diagnostic kit for use in detecting the presence in a canine subject of at least one genetic marker that is genetically linked and co-segregating with a progressive rod-cone degeneration disease trait, comprising at least one oligonucleotide selected from the group consisting of SEQUENCE ID NO: 9, SEQUENCE ID NO: 10, SEQUENCE ID NO: 11, SEQUENCE ID NO: 12, SEQUENCE ID NO: 13, SEQUENCE ID NO: 14, SEQUENCE ID NO: 15, SEQUENCE ID NO: 16, SEQUENCE ID NO: 17, SEQUENCE ID NO: 18, SEQUENCE ID NO: 19, SEQUENCE ID NO: 20, SEQUENCE ID NO: 21, SEQUENCE ID NO: 30, SEQUENCE ID NO: 31, and combinations thereof.

39. The diagnostic kit of claim 38 further comprising at least one additional reagent selected from the group consisting of a lysing buffer for lysing cells contained in the specimen; enzyme amplification reaction components dNTPs, reaction buffer, and amplifying enzyme; and a combination of the additional reagents.

* * * * *